(12) United States Patent
Von Der Fecht et al.

(10) Patent No.: US 7,658,936 B2
(45) Date of Patent: Feb. 9, 2010

(54) COSMETIC OR DERMATOLOGICAL IMPREGNATED CLOTHS

(75) Inventors: Stephanie Von Der Fecht, Schenefeld (DE); Jörg Küther, Pinneberg (DE)

(73) Assignee: Goldschmidt GmbH (DE)

( * ) Notice: Subject to any disclaimer, the term of this patent is extended or adjusted under 35 U.S.C. 154(b) by 993 days.

(21) Appl. No.: 10/745,066

(22) Filed: Dec. 22, 2003

(65) Prior Publication Data

US 2004/0191300 A1    Sep. 30, 2004

Related U.S. Application Data

(63) Continuation of application No. PCT/EP02/06725, filed on Jun. 18, 2002.

(30) Foreign Application Priority Data

Jun. 21, 2001    (DE) .................... 101 29 973

(51) Int. Cl.
    A01N 25/34    (2006.01)
    A01N 8/02     (2006.01)
    A61F 13/00    (2006.01)

(52) U.S. Cl. ............... 424/402; 424/401; 424/443

(58) Field of Classification Search .......... 424/402
    See application file for complete search history.

(56) References Cited

U.S. PATENT DOCUMENTS

| | | | | |
|---|---|---|---|---|
| 4,142,017 A | * | 2/1979 | Blackburn et al. | 428/284 |
| 5,230,949 A | * | 7/1993 | Howard et al. | 442/365 |
| 5,770,185 A | * | 6/1998 | Wachter et al. | 424/65 |
| 5,871,762 A | * | 2/1999 | Venkitaraman et al. | 424/402 |
| 5,980,924 A | * | 11/1999 | Yamazaki et al. | 424/402 |
| 6,149,926 A | | 11/2000 | Venkitaraman et al. | |
| 6,248,338 B1 | * | 6/2001 | Muller et al. | 424/401 |
| 6,306,408 B1 | * | 10/2001 | Eichhorn et al. | 424/401 |
| 6,436,414 B1 | * | 8/2002 | Raschke et al. | 424/401 |
| 6,641,822 B2 | | 11/2003 | Eichhorn et al. | |
| 2003/0012801 A1 | | 1/2003 | Raschke et al. | |
| 2004/0086538 A1 | | 5/2004 | Sauermann et al. | |

FOREIGN PATENT DOCUMENTS

| | | |
|---|---|---|
| DE | 197 11 452 A1 | 9/1998 |
| DE | 198 02 206 A | 7/1999 |
| DE | 198 60 267 A1 | 6/2000 |
| DE | 299 04 320 U 1 | 10/2000 |
| DE | 199 41 769 A1 | 3/2001 |
| DE | 199 43 678 A1 | 3/2001 |
| DE | 100 31 703 A1 | 1/2002 |

OTHER PUBLICATIONS

Graco/Liquid Control;Viscosity,8400 Port Jackson Ave NW—North Canton, Ohio 44720 Phone: 330-494-1313, 2007, printed pp. 1-4, especially p. 1).*
International Search Report from corresponding International Application No. PCT/EP02/06725 dated Jun. 18, 2002.
German search report for application No. 101 29 973.7, dated Jan. 13, 2003.

* cited by examiner

Primary Examiner—Sreeni Padmanabhan
Assistant Examiner—Timothy E Betton
(74) Attorney, Agent, or Firm—Alston & Bird LLP

(57) ABSTRACT

The invention is a cosmetic or dermatological cloth, comprising a water-insoluble nonwoven material, which is moistened with a cosmetic or dermatological impregnating solution comprising an oil-in-water emulsions having a viscosity of less than 2000 mPa·s and comprising one or more partially neutralized glyceride esters selected from the group consisting of monoglyceride and diglyceride esters of saturated fatty acids with citric acid and one or more fatty alcohols selected from the group consisting of branched and unbranched alkyl alcohols with 12 to 40 carbon atoms.

25 Claims, No Drawings

COSMETIC OR DERMATOLOGICAL IMPREGNATED CLOTHS

CROSS-REFERENCE TO RELATED APPLICATIONS

This is a continuation application of PCT/EP02/06725, filed Jun. 18, 2002, which is incorporated herein by reference in its entirety, and also claims the benefit of German Priority Application No. 101 29 973.7, filed Jun. 21, 2001.

FIELD OF THE INVENTION

The invention relates to cosmetic and dermatological cloths. More specifically, the present invention relates to cosmetic and dermatological cloths which have been moistened with low-viscosity cosmetic and dermatological impregnation solutions, in particular with low-viscosity cosmetic and dermatological impregnation solutions which have long-term stability. In particular, the invention relates to cosmetic and dermatological impregnated, optionally surface-structured care, cleansing and deodorizing cloths, and to impregnated cloths for controlling skin diseases (such as acne etc.) and those which care for the skin in a targeted manner following sunburn and reduce the secondary reactions of the skin to the effect of UV radiation. In addition, the present invention relates to impregnation solutions which are suitable for impregnating cloths of this kind.

BACKGROUND OF THE INVENTION

Impregnated cloths are used widely in very diverse areas as articles of everyday use. They permit, inter alia, efficient and mild cleansing and care, particularly also in the absence of (running) water.

In this connection, the actual article of use consists of two components:
  a) a dry cloth constructed from materials such as paper and/or a very wide variety of mixtures of natural or synthetic fibers and
  b) a low-viscosity impregnation solution.

Cosmetic or dermatological cloths may consist either of water-soluble materials (e.g. toilet paper) or water-insoluble materials. In addition, the cloths may be smooth or surface-structured. Surface-structured cloths are prepared e.g. on the basis of cellulose and are used in particular as household cloths and for perianal cleaning. Their structure is produced by mechanical embossing by means of calender rolls. Such cloths have low tear resistance coupled with high roughness and hardness. They are therefore only of limited suitability for use on the human skin.

Conventional impregnation solutions for water-insoluble nonwoven materials have hitherto frequently had the problem of low long-term stability. Such formulations have a tendency toward phase separation, particularly at elevated ambient temperature, which represents a decisive disadvantage for the impregnation process and also for the final quality of the end product.

The long-term stability of impregnation solutions of the prior art is generally ensured through the use of increased emulsifier concentrations, and considerable energy input—for example during homogenization.

SUMMARY OF THE INVENTION

An object of the present invention was therefore to find impregnation solutions which have long-term stability to apply to water-insoluble nonwoven materials which do not have the disadvantages of the prior art and which represent low-viscosity emulsions which have long-term stability, even where the emulsifier contents are low, and, where possible, do not have to be homogenized.

It was surprising and could not have been foreseen by the person skilled in the art that cosmetic and dermatological cloths, where the cloths consist of a water-insoluble nonwoven, which have been moistened with cosmetic and dermatological impregnation solutions which
  a. represent DNV emulsions which
  b. have a viscosity of less than 2000 mPa·s, and which
  c. comprise one or more partially neutralized monoglyceride and/or diglyceride esters of saturated fatty acids with citric acid and
  d. one or more fatty alcohols chosen from the group of branched and unbranched alkyl alcohols with 12 to 40 carbon atoms,
overcome the disadvantages of the prior art.

DETAILED DESCRIPTION OF THE PREFERRED EMBODIMENTS

The cloths according to the invention represent combinations of a soft, water-insoluble nonwoven material with low-viscosity cosmetic and dermatological impregnation solutions. They are entirely satisfactory from any viewpoint and are accordingly very particularly suitable for serving as a basis for preparation forms with diverse applications. The cloths according to the invention exhibit very good sensory and cosmetic properties and are also distinguished by excellent skincare data.

The nonwoven material is preferably consolidated as spun lace material in the preparation process by water jets. The cloths according to the invention may be either structured or unstructured ("smooth"). If the material is to be structured, the structuring advantageously likewise takes place by means of water jets. This structuring produces, for example, a uniform sequence of elevations and indentations in the material.

In combination with suitable impregnation solutions, a structuring of this kind permits, as a result of its elevations, both better access to depressions in the human skin and also, as a result of its structural values, increased soil-uptake capacity. This leads overall to a significantly improved cleaning performance.

In addition, better access to depressions in the human skin is of particular importance for controlling skin diseases and skin irritations and for effectively displaying a deodorizing action.

Thus, according to the invention, structured cosmetic or dermatological cloths are particularly preferred.

The cosmetic and dermatological impregnation solutions with which the cloths according to the invention have been moistened can be in various forms. They are preferably low-viscosity, in particular sprayable and have e.g. a viscosity of less than 2000 mPa·s, in particular, less than 1500 mPa·s (measuring instrument: Haake Viskotester VT-02 at 25° C.).

A particularly advantageous citrate for the purposes of the present invention is glyceryl stearate citrate. Such citrates are available, for example, under the product name "IMWITOR® 370" from Hüls AG or "Axol 62" from Goldschmidt AG.

The total amount of one or more citrates according to the invention in the finished cosmetic or dermatological impregnation solutions is advantageously chosen from the range from 0.1 to 10.0% by weight, preferably 0.5 to 6.0% by weight, in each case based on the total weight of the impregnation solutions.

According to the invention, fatty alcohols with a chain length of from 10 to 30 carbon atoms are advantageous. Particular preference is given to cetyl, stearyl and/or cetearyl alcohol (a mixture of 1-hexadecanol and 1-octadecanol in equal amounts).

The total amount of one or more fatty alcohols used according to the invention in the finished cosmetic or dermatological impregnation solutions is advantageously chosen from the range from 0.1 to 10.0% by weight, preferably 0.5 to 6.0% by weight, in each case based on the total weight of the impregnation solutions.

It may in some instances be advantageous for the purposes of the present invention to incorporate further emulsifiers or coemulsifiers into the cosmetic or dermatological impregnation solutions according to the invention, for example in order to further improve the stability of the impregnation solutions.

Advantageous further emulsifiers for the purposes of the present invention are, for example, silicone emulsifiers, phosphate emulsifiers and/or ethoxylated emulsifiers.

It is advantageous according to the invention to choose the weight ratios of citrates (one or more compounds) to fatty alcohols (one or more compounds) from 7:3 to 3:7, preferably from 2:1 to 1:2,1 particularly preferably about 1:1.

According to the invention, it is possible and advantageous to freely choose the proportion of the oil phase of the impregnation solutions according to the invention in the range from 5 to 40% by weight, based on the total weight of the impregnation solutions.

The main constituents of the impregnation solutions of the present invention which can be used are:
  water or aqueous solution;
  oils, such as capric or caprylic acid triglycerides, but preferably castor oil
  fats, waxes and other natural and synthetic fatty substances, preferably esters of fatty acids with alcohols of low carbon number, e.g. with isopropanol, propylene glycol or glycerol, or esters of fatty alcohols with alkanoic acids of low carbon number or with fatty acids
  alcohols, diols or polyols of low carbon number, and ethers thereof, preferably ethanol, isopropanol, propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products.

In particular, mixtures of the aforementioned solvents are used. In the case of alcoholic solvents, water may be a further constituent.

The water phase(s) of the impregnation solution may advantageously comprise customary cosmetic auxiliaries, such as, for example polymers, foam stabilizers, electrolytes, sugar derivatives and/or moisturizers.

Moisturizers is the term used to describe substances or mixtures of substances which, following application or distribution on the surface of the skin, confer on cosmetic or dermatological impregnation solutions the property of reducing the moisture loss by the horny layer (also called transepidermal water loss (TEWL)) and/or have a beneficial effect on the hydration of the horny layer.

Advantageous moisturizers for the purposes of the present invention are, for example, glycerol, lactic acid, pyrrolidonecarboxylic acid and urea. In addition, it is particularly advantageous to use polymeric moisturizers from the group of polysaccharides which are soluble in water and/or swellable in water and/or gellable using water. Particularly advantageous are, for example, hyaluronic acid, chitosan and/or a fucose-rich polysaccharide which is listed in Chemical Abstracts under the registry number 178463-23-5 and is available, for example, under the name Fucogel®1000 from SOLABIA S.A.

If the impregnation solution comprises one or more oil phases, the oil(s) is/are advantageously chosen for the purposes of the present invention from the group of esters of saturated and/or unsaturated, branched and/or unbranched alkanecarboxylic acids having a chain length of from 3 to 30 carbon atoms and saturated and/or unsaturated, branched and/or unbranched alcohols having a chain length of from 3 to 30 carbon atoms, from the group of esters of aromatic carboxylic acids and saturated and/or unsaturated, branched and/or unbranched alcohols having a chain length of from 3 to 30 carbon atoms. Such ester oils can then advantageously be chosen from the group consisting of isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethylhexyl laurate, 2-hexyldecyl stearate, 2-octyidodecyl palmitate, oleyl oleate, oleyl erucate, erucyl oleate, erucyl erucate, and synthetic, semisynthetic and natural mixtures of such esters, e.g. jojoba oil.

In addition, the oils can advantageously be chosen from the group of branched and unbranched hydrocarbons and hydrocarbon waxes, silicone oils, dialkyl ethers, the group of saturated or unsaturated, branched or unbranched alcohols, and fatty acid triglycerides, namely the triglycerol esters of saturated and/or unsaturated, branched and/or unbranched alkanecarboxylic acids having a chain length of from 8 to 24, in particular 12 to 18 carbon atoms. The fatty acid triglycerides can, for example, advantageously be chosen from the group of synthetic, semisynthetic and natural oils, e.g. olive oil, sunflower oil, soybean oil, peanut oil, rapeseed oil, almond oil, palm oil, coconut oil, palm kernel oil and the like.

Any mixtures of such oil and wax components can also advantageously be used for the purposes of the present invention.

The oils are advantageously chosen from the group consisting of 2-ethylhexyl isostearate, octyldodecanol, isotridecyl isononanoate, isoeicosane, 2-ethylhexyl cocoate, $C_{12-15}$-alkyl benzoate, caprylic/capric triglyceride and dicaprylyl ether.

Particularly advantageous mixtures are those of $C_{12-15}$-alkyl benzoate and 2-ethylhexyl isostearate, those of $C_{12-15}$-alkyl benzoate and isotridecyl isononanoate, and those of $C_{12-15}$-alkyl benzoate, 2-ethylhexyl isostearate and isotridecyl isononanoate.

Of the hydrocarbons, paraffin oil, squalane and squalene are advantageously to be used for the purposes of the present invention.

The oil phase can advantageously further have a content of cyclic or linear silicone oils or consist entirely of such oils, as a result of which SAN (silicone-in-water) formulations, for example, arise. However, apart from the silicone oil or the silicone oils, it is preferred to use an additional content of other oil phase components.

Cyclomethicone (octamethylcyclotetrasiloxane) is advantageously used as silicone oil to be used according to the invention. However, other silicone oils can also advantageously be used for the purposes of the present invention, for example hexamethylcyclotrisiloxane, polydimethylsiloxane and poly(methylphenylsiloxane).

Also particularly advantageous are mixtures of cyclomethicone and isotridecyl isononanoate, and of cyclomethicone and 2-ethylhexyl isostearate.

The oil(s) is/are also advantageously chosen from the group of phospholipids. The phospholipids are phosphoric esters of acylated glycerol. The most significant phosphatidylcholines are, for example, the lecithins, which are distinguished by the general structure

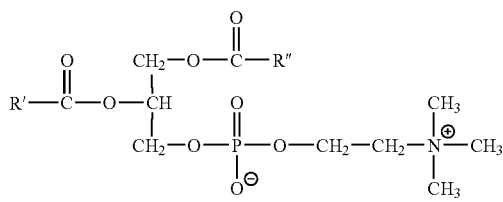

where R' and R" are typically unbranched aliphatic radicals having 15 or 17 carbon atoms and up to 4 cis double bonds.

For the purposes of the present invention, the cloths advantageously comprise one or more washing-active surfactants from the following four groups A to D, in particular if they are to be used as cleansing cloths:

A. Anionic surfactants

Anionic surfactants to be used advantageously are acylamino acids (and salts thereof), such as 1. acylglutamates, for example sodium acylglutamate, di-TEA-palmitoyl aspartate and sodium caprylic/capric glutamate, 2. acylpeptides, for example palmitoyl hydrolyzed milk protein, sodium cocoyl hydrolyzed soya protein and sodium/potassium cocoyl hydrolyzed collagen, 3. sarcosinates, for example myristoyl sarcosine, TEA-lauroyl sarcosinate, sodium lauroyl sarcosinate and sodium cocoyl sarcosinate, 4. taurates, for example sodium lauroyl taurate and sodium methyl cocoyl taurate, carboxylic acids and derivatives, such as 1. carboxylic acids, for example lauric acid, aluminum stearate, magnesium alkanolate and zinc undecylenate, 2. ester carboxylic acids, for example calcium stearoyl lactylate, laureth-6 citrate and sodium PEG4 lauramide carboxylate, 3. ether carboxylic acids, for example sodium laureth-13 carboxylate and sodium PEG-6 cocamide carboxylate, phosphoric acid esters and salts, such as, for example, DEA-oleth-10 phosphate and dilaureth4 phosphate, sulfonic acids and salts, such as 1. acyl isethionates, e.g. sodium/ammonium cocoyl isethionate, 2. alkylarylsulfonates, 3. alkylsulfonates, for example sodium cocosmonoglyceride sulfate, sodium $C_{12-14}$-olefinsulfonate, sodium lauryl sulfoacetate and magnesium PEG-3 cocamide sulfate, 4. sulfosuccinates, for example dioctyl sodium sulfosuccinate, disodium laureth sulfosuccinate, disodium lauryl sulfosuccinate and disodium undecylenamido-MEA sulfosuccinate and sulfuric esters, such as 1. alkyl ether sulfate, for example sodium, ammonium, magnesium, MIPA, TIPA laureth sulfate, sodium myreth sulfate and sodium $C_{12-13}$ pareth sulfate, 2. alkyl sulfates, for example sodium, ammonium and TEA laurylsulfate.

B. Cationic surfactants

Cationic surfactants to be used advantageously are 1. alkylamines, 2. alkylimidazoles, 3. ethoxylated amines and 4. quaternary surfactants.

Quaternary surfactants contain at least one N atom which is bonded covalently to 4 alkyl or aryl groups. Irrespective of the pH, this leads to a positive charge. Benzalkonium chloride, alkylbetaine, alkylamidopropylbetaine and alkylamidopropylhydroxysultaine are advantageous.

C. Amphoteric surfactants

Amphoteric surfactants to be used advantageously are 1. acyl/dialkylethylenediamine, for example sodium acylamphoacetate, disodium acylamphodipropionate, disodium alkylamphodiacetate, sodium acylamphohydroxypropylsulfonate, disodium acylamphodiacetate and sodium acylamphopropionate, 2. N-alkylamino acids, for example aminopropylalkylglutamide, alkylaminopropionic acid, sodium alkylimidodipropionate and lauroamphocarboxyglycinate.

D. Nonionic surfactants

Nonionic surfactants to be used advantageously are 1. alcohols, 2. alkanolamides, such as cocoamides MEA/DEA/MIPA, 3. amine oxides, such as cocamidopropylamine oxide, 4. esters which are formed by esterification of carboxylic acids with ethylene oxide, glycerol, sorbitan or other alcohols, 5. ethers, for example ethoxylated alcohols, ethoxylated lanolin, ethoxylated polysiloxanes, propoxylated POE ethers and alkyl polyglycosides, such as lauryl glucoside, decyl glycoside and cocoglycoside.

The impregnation solutions particularly advantageously comprise one or more washing-active surfactants from the group of surfactants which have an HLB value of more than 25, very particularly those which have an HLB value of more than 35.

For the purposes of the present invention, it is advantageous if the content of one or more washing-active surfactants in the cosmetic or dermatological impregnation solution is chosen from the range from 5 to 25% by weight, very particularly advantageously from 10 to 15% by weight, in each case based on the total weight of the impregnation solution.

Furthermore, the impregnation solutions for the cosmetic and dermatological cloths according to the invention also advantageously comprise preservatives.

Preservatives are antimicrobial substances which are added during the preparation process to a product (foods or confectionery, pharmaceutical, cosmetic or also chemicotechnical preparations) in small amounts (usually between about 0.0005% and 1% active content, depending on the product). Preservatives are intended to protect products during preparation, storage and use against contamination by microorganisms, in particular against detrimental changes caused microbially.

A preservative is, in principle, subject to the following requirements: it must be sufficiently antimicrobially effective, technologically applicable and safe with regard to health. The aspect of safety with regard to health must, however, also be satisfied by the finished preparation, the commercial product. In this connection, it is to be taken into consideration that microorganisms may be present in e.g. cosmetic products primarily as a result of production, or may secondarily be passed into the cosmetic product by the consumer.

For this reason, it must be ensured that the finished product is also safe over the entire use period.

Most preservatives intended or proposed for preservation have a bacteriostatic and fungistatic action, sometimes also a bactericidal and fungicidal action: they should be odorless and tasteless and, in the doses used, as far as possible be soluble, nontoxic, skin-compatible and sufficiently effective. The preservatives must, in order to be effective, be dissolved in the crude material or auxiliary to be preserved. Since most preservatives are more soluble in fat than water, it must be taken into account that e.g. in an emulsion whose aqueous phase is to be preserved, the preservative incorporated into the aqueous phase migrates into the fatty phase over the course of storage, thus jeopardizing preservation of the aqueous phase. For this reason, it is advisable to use a combination of preservatives, i.e. to preserve the aqueous phase with a preservative which is readily soluble in water, but at the same time to preserve the fatty phase with a preservative which is soluble in fat.

Although sterility is not generally required for a cosmetic preparation, it must, however, be free from pathogenic microbes and be protected from changes caused microbially.

It should be taken into consideration that different types of emulsion, aqueous solutions, suspensions etc. require different preservation, that the preserving action of individual preservatives is dependent on the composition and the physical properties of the preparation to be preserved, that interactions between the preservative, the active ingredients and auxiliaries are to be taken into account, that various active ingredients or auxiliaries can adsorb preservatives and thus possibly deactivate them, that, in particular, hydrocolloids present in the preparation may, depending on the concentration, hinder the antimicrobial activity of preservatives and that, finally, again depending on the concentration and the type of preservative, the stratum corneum adsorbs the preservative, this then possibly leading to permeation and absorption of the preservative.

Preservatives permitted in food technology which can also be advantageously used for the purposes of the present invention are listed below with their E numbers.

| | |
|---|---|
| E 200 | Sorbic acid |
| E 201 | Sodium sorbate |
| E 202 | Potassium sorbate |
| E 203 | Calcium sorbate |
| E 210 | Benzoic acid |
| E 211 | Sodium benzoate |
| E 212 | Potassium benzoate |
| E 213 | Calcium benzoate |
| E 214 | p-Hydroxybenzoic ethyl ester |
| E 215 | p-Hydroxybenzoic ethyl ester Na salt |
| E 216 | p-Hydroxybenzoic n-propyl ester |
| E 217 | -Hydroxybenzoic n-propyl ester Na salt |
| E 218 | p-Hydroxybenzoic methyl ester |
| E 219 | p-Hydroxybenzoic methyl ester Na salt |
| E 220 | Sulfur dioxide |
| E 221 | Sodium sulfite |
| E 222 | Sodium hydrogensulfite |
| E 223 | Sodium disulfite |
| E 224 | Potassium disulfite |
| E 226 | Calcium sulfite |
| E 227 | Calcium hydrogensulfite |
| E 228 | Potassium hydrogensulfite) |
| E 230 | Biphenyl (diphenyl) |
| E 231 | Orthophenylphenol |
| E 232 | Sodium orthophenylphenoxide |
| E 233 | Thiabendazole |
| E 235 | Natamycin |
| E 236 | Formic acid |
| E 237 | Sodium formate |
| E 238 | Calcium formate |
| E 239 | Hexamethylenetetramine |
| E 249 | Potassium nitrite |
| E 250 | Sodium nitrite |
| E 251 | Sodium nitrate |
| E 252 | Potassium nitrate |
| E 280 | Propionic acid |
| E 281 | Sodium propionate |
| E 282 | Calcium propionate |
| E 283 | Potassium propionate |
| E 290 | Carbon dioxide |

Also advantageous are preservatives or preservative auxiliaries customary in cosmetics, such as dibromodicyanobutane (2-bromo-2-bromomethylglutarodinitrile), phenoxyethanol, 3-iodo-2-propynyl butylcarbamate, 2-bromo-2-nitropropane-1,3-diol, imidazolidinylurea, 5-chloro-2-methyl4-isothiazolin-3-one, 2-chloroacetamide, benzalkonium chloride, benzyl alcohol.

For the purposes of the present invention, particularly advantageous cosmetic impregnation solutions further obtain antioxidants as additives or active ingredients. According to the invention, the impregnation solutions advantageously comprise one or more antioxidants. Favorable, but nevertheless optional antioxidants which may be used are all antioxidants customary or suitable for cosmetic and/or dermatological applications.

The antioxidants are advantageously chosen from the group consisting of amino acids (e.g. glycine, histidine, tyrosine, tryptophan) and derivatives thereof, imidazoles (e.g. urocaninic acid) and derivatives thereof, peptides such as D,L-carnosine, D-carnosine, L-carnosine and derivatives thereof (e.g. anserine), carotenoids, carotenes (e.g. α-carotene, β-carotene, lycopene) and derivatives thereof, lipoic acid and derivatives thereof (e.g. dihydrolipoic acid), aurothioglucose, propylthiouracil and other thiols (e.g. thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts) and sulfoximine compounds (e.g. buthionine sulfoximines, homocysteine sulfoximine, buthionine sulfones, penta-, hexa-,heptathionine sulfoximine) in very low tolerated doses (e.g. μmol to zmol/kg), and also (metal) chelating agents (e.g. α-hydroxy fatty acids, palmitic acid, phytic acid, lactoferrin), α-hydroxy acids (e.g. citric acid, lactic acid, malic acid), humic acid, bile acid, bile extracts, bilirubin, biliverdin, EDTA, EGTA and derivatives thereof, unsaturated fatty acids and derivatives thereof (e.g. γ-linolenic acid, linoleic acid, oleic acid), folic acid and derivatives thereof, ubiquinone and ubiquinol and derivatives thereof, vitamin C and derivatives (e.g. ascorbyl palmitate, Mg ascorbyl phosphate, ascorbyl acetate), tocopherols and derivatives (e.g. vitamin E acetate), vitamin A and derivatives (vitamin A palmitate) and conyferyl benzoate of benzoin resin, rutinic acid and derivatives thereof, ferulic acid and derivatives thereof, butylhydroxy toluene, butylhydroxy anisole, nordihydroguaiacic acid, nordihydroguaiaretic acid, trihydroxybutyrophenone, uric acid and derivatives thereof, mannose and derivatives thereof, zinc and derivatives thereof (e.g. ZnO, ZnSO$_4$), selenium and derivatives thereof (e.g. selenomethionine), stilbenes and derivatives thereof (e.g. stilbene oxide, trans-stilbene oxide) and the derivatives (salts, esters, ethers, sugars, nucleotides, nucleosides, peptides and lipids) of these active ingredients which are suitable according to the invention.

For the purposes of the present invention, water-soluble antioxidants can be used particularly advantageously.

Preferred active ingredients are antioxidants which are able to protect the skin from oxidative stress. Particularly preferred antioxidants here are vitamin E and derivatives thereof, and vitamin A and derivatives thereof.

The amount of antioxidants (one or more compounds) in the impregnation solutions is preferably 0.001 to 30% by weight, particularly preferably 0.05 to 20% by weight, in particular 0.1 to 10% by weight, based on the total weight of the preparation.

If vitamin E and/or derivatives thereof are the antioxidant(s), it is advantageous to choose their respective concentrations from the range from 0.001 to 10% by weight, based on the total weight of the formulation.

If vitamin A or vitamin A derivatives, or carotenes or derivatives thereof are the antioxidant(s), it is advantageous to choose their respective concentrations from the range from 0.001 to 10% by weight, based on the total weight of the formulation.

The active ingredients (one or more compounds) can also very advantageously be chosen according to the invention from the group of lipophilic active ingredients, in particular from the following group: acetylsalicylic acid, atropine, azulene, hydrocortisone and derivatives thereof, e.g. hydrocortisone-17 valerate, vitamins, e.g. ascorbic acid and derivatives thereof, vitamins of the B and D series, very favorably vitamin $B_1$, vitamin $B_{12}$ and vitamin $D_1$, but also bisabolol, unsaturated fatty acids, namely the essential fatty acids (often also called a vitamin F), in particular gamma-linolenic acid, oleic acid, eicosapentaenoic acid, docosahexaenoic acid and derivatives thereof, chloroamphenicol, caffeine, prostaglandins, thymol, camphor, extracts or other products of a vegetable and animal origin, e.g. evening primrose oil, borage oil or currant seed oil, fish oils, cod-liver oil and also ceramides and ceramide-like compounds, etc.

It is also advantageous to choose the active ingredients from the group of refatting substances, for example purcellin oil, Eucerit® and Neocerit®.

The active ingredient(s) is/are also particularly advantageously chosen from the group of NO synthase inhibitors, particularly if the impregnation solutions according to the invention are to be used for the treatment and prophylaxis of the symptoms of intrinsic and/or extrinsic skin ageing and for the treatment and prophylaxis of the harmful effects of ultraviolet radiation on the skin. A preferred NO synthase inhibitor is nitroarginine.

Accordingly, impregnated cloths for the purposes of the present invention are suitable particularly advantageously for the prophylaxis and treatment of cosmetic or dermatological skin changes, as occur e.g. during skin ageing. They are also advantageously suitable for the symptoms of dry or rough skin.

Skin ageing is caused e.g. by endogenous, genetically determined factors. As a result of ageing, the epidermis and dermis experience e.g. the following structural damage and functional disorders, which can also be covered by the term "senile xerosis":

a) dryness, roughness and formation of (dryness) wrinkles,
b) itching and
c) reduced refatting by sebaceous glands (e.g. after washing).

Exogenous factors, such as UV light and chemical noxae, can have a cumulative effect and, for example, accelerate or add to the endogenous ageing processes. The epidermis and dermis experience, in particular as a result of exogenous factors, e.g. the following structural damage and functional disorders in the skin, which go beyond the degree and quality of the damage in the case of chronological ageing:

d) visible vascular dilation (telangiectases, cuperosis);
e) flaccidity and formation of wrinkles;
f) local hyperpigmentation, hypopigmentation and abnormal pigmentation (e.g. age spots) and
g) increased susceptibility to mechanical stress (e.g. cracking).

In a particular embodiment, the present invention relates in particular to products for the care of skin aged naturally, and to the treatment of secondary damage of photoageing, in particular of the phenomena listed under a) to g).

The active ingredient(s) is/are also advantageously chosen from the group which includes catechins and bile esters of catechins and aqueous or organic extracts from plants or parts of plants which have a content of catechins or bile esters of catechins, such as, for example, the leaves of the Theaceae plant family, in particular of the species *Camellia sinensis* (green tea). Particularly advantageous are typical ingredients thereof (such as e.g. polyphenols or catechins, caffeine, vitamins, sugar, minerals, amino acids, lipids).

Catechins are a group of compounds which are to be regarded as hydrogenated flavones or anthocyanidines and are derivatives of "catechin" (catechol, 3,3',4',5,7-flavanpentaol, 2-(3,4-dihydroxyphenyl)chroman-3,5,7-triol). Epicatechin ((2R,3R)-3,3',4',5,7-flavan-pentaol) is also an advantageous active ingredient for the purposes of the present invention.

Also advantageous are plant extracts with a content of catechins, in particular extracts of green tea, such as e.g. extracts from leaves of plants of the species Camellia spec., very particularly the types of tea *Camellia sinenis, C. assamica, C. taliensis* and *C. irrawadiensis* and hybrids of these with, for example, *Camellia japonica*.

Preferred active ingredients are also polyphenols or catechins from the group (−)-catechin, (+)-catechin, (−)-catechin gallate, (−)-gallocatechin gallate, (+)-epicatechin, (−)-epicatechin, (−)-epicatechin gallate, (−)-epigallocatechin and (−)-epigallocatechin gallate.

Flavone and its derivatives (also often collectively called "flavones") are also advantageous active ingredients for the purposes of the present invention. They are characterized by the following basic structure (substitution positions are shown):

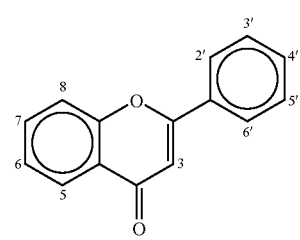

Some of the more important flavones which can also preferably be used in impregnation solutions according to the invention are given in the table below:

| | OH substitution positions | | | | | | | |
|---|---|---|---|---|---|---|---|---|
| | 3 | 5 | 7 | 8 | 2' | 3' | 4' | 5' |
| Flavone | − | − | − | − | − | − | − | − |
| Flavonol | + | − | − | − | − | − | − | − |
| Chrysin | − | + | + | − | − | − | − | − |
| Galangin | + | + | + | − | − | − | − | − |
| Apigenin | − | + | + | − | − | − | + | − |
| Fisetin | + | − | + | − | − | + | + | − |
| Luteolin | − | + | + | − | − | + | + | − |
| Kaempferol | + | + | + | − | − | − | + | − |
| Quercetin | + | + | + | − | − | + | + | − |
| Morin | + | + | + | − | + | − | + | − |
| Robinetin | + | − | + | − | − | + | + | + |
| Gossypetin | + | + | + | + | − | + | + | − |
| Myricetin | + | + | + | − | − | + | + | + |

In nature, flavones are usually in glycosylated form.

According to the invention, the flavonoids are preferably chosen from the group of substances of the generic structural formula

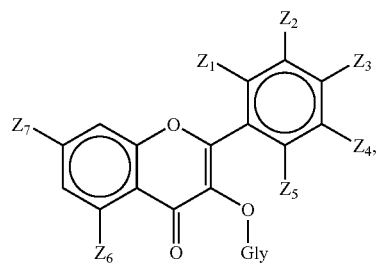

where $Z_1$ to $Z_7$, independently of one another, are chosen from the group consisting of H, OH, alkoxy and hydroxyalkoxy, where the alkoxy and hydroxyalkoxy groups can be branched or unbranched and have 1 to 18 carbon atoms, and where Gly is chosen from the group of mono- and oligoglycoside radicals.

According to the invention, the flavonoids can however, also advantageously be chosen from the group of substances of the generic structural formula

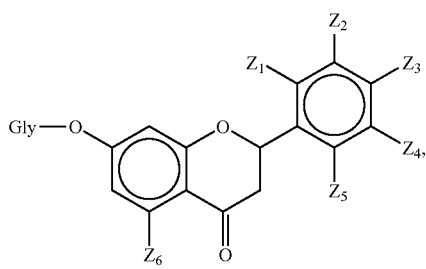

where $Z_1$ to $Z_6$, independently of one another, are chosen from the group consisting of H, OH, alkoxy and hydroxyalkoxy, where the alkoxy and hydroxyalkoxy groups may be branched or unbranched and have 1 to 18 carbon atoms, where Gly is chosen from the group mono and oligoglycoside radicals.

Preferably, such structures can be chosen from the group of substances of the generic structural formula

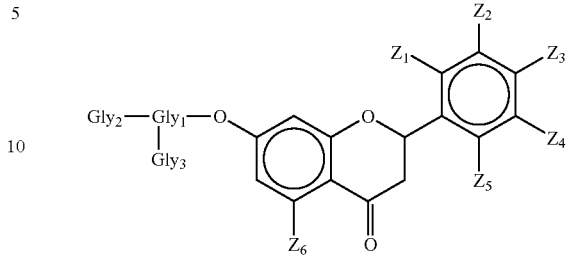

where $Gly_1$, $Gly_2$ and $Gly_3$, independently of one another, are monoglycoside radicals or. $Gly_2$ and $Gly_3$ may also, individually or together, represent saturations by hydrogen atoms.

Preferably, $Gly_1$, $Gly_2$ and $Gly_3$, independently of one another, are chosen from the group of hexosyl radicals, in particular the rhamnosyl radicals and glucosyl radicals. However, hexosyl radicals, for example allosyl, altrosyl, galactosyl, gulosyl, idosyl, mannosyl and talosyl, can also be used advantageously in some circumstances. It may also be advantageous according to the invention to use pentosyl radicals.

$Z_1$ to $Z_5$ are, independently of one another, advantageously chosen from the group consisting of H, OH, methoxy, ethoxy and 2-hydroxyethoxy, and the flavone. glycosides have the structure

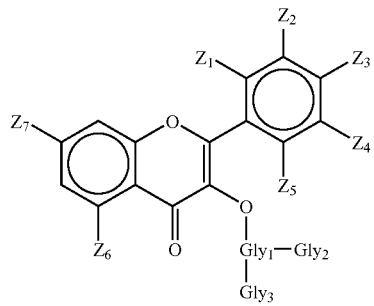

The flavone glycosides according to the invention are particularly advantageously from the group given by the following structure:

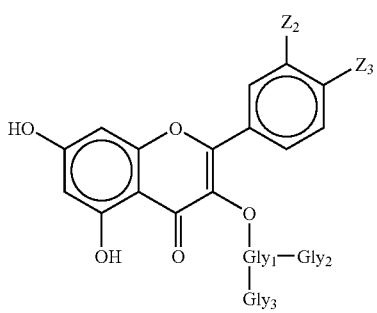

where $Gly_1$, $Gly_2$ and $Gly_3$, independently of one another, are monoglycoside radicals or. $Gly_2$ and $Gly_3$ can also, individually or together, represent saturations by hydrogen atoms.

Preferably, $Gly_1$, $Gly_2$ and $Gly_3$, independently of one another, are chosen from the group of hexosyl radicals, in particular of rhamnosyl radicals and glucosyl radicals. However, other hexosyl radicals, for example allosyl, altrosyl, galactosyl, gulosyl, idosyl, mannosyl and talosyl, can also advantageously be used in some circumstances. It may also be advantageous according to the invention to use pentosyl radicals.

For the purposes of the present invention, it is particularly advantageous to choose the flavone glucoside(s) from the group consisting of α-glucosylrutin, α-glucosylmyricetin, α-glucosylisoquercitrin, α-glucosylisoquercetin and α-glucosylquercitrin.

Particular preference is given according to the invention to α-glucosylrutin.

Also advantageous according to the invention are naringin (aurantin naringenin-7-rhamno-glucoside), hesperidin 3',5,7-trihydroxy-4'-methoxyflavanone-7-rutinoside, hesperidoside, hesperetin-7-O-rutinoside). rutin (3,3',4',5,7-pentahydroxyflyvone-3-rutinoside, quercetin-3-rutinoside, sophorin, birutan, rutabion, taururtin, phytomelin, melin), troxerutin (3,5-dihydroxy-3',4',7-tris(2-hydroxyethoxy)flavone-3-(6-O-(6-deoxy-α-L-mannopyranosyl)-β-D-glucopyranoside)), monoxerutin (3,3',4',5-tetrahydroxy-7-(2-hydroxyethoxy) flavone-3-(6-O-(6-deoxy-α-L-mannopyranosyl)-β-D-glucopyranoside)), dihydrorobinetin (3,3',4',5',7-pentahydroxyflavanone), taxifolin (3,3',4',5,7-pentahydroxyflavanone), eriodictyol-7-glucoside (3',4',5,7-tetrahydroxyflavanone-7 glucoside), flavanomarein (3',4',7,8-tetrahydroxyflavanone-7 glucoside) and isoquercetin (3,3',4',5,7-pentahydroxyflavanone-3-(β-D-glucopyranoside).

It is also advantageous to choose the active ingredient(s) from the group of ubiquinones and plastoquinones.

Ubiquinones are distinguished by the structural formula

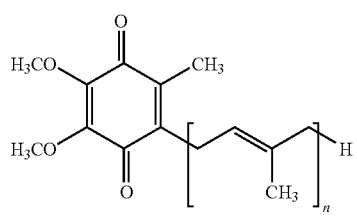

and are the most widespread and thus the most investigated bioquinones. Ubiquinones are referred to depending on the number of isoprene units linked in the side chain as Q-1, Q-2, Q-3 etc., or according to the number of carbon atoms, as U-5, U-10, U-15 etc. They preferably appear with certain chain lengths, e.g. in some microorganisms and yeasts where n=6. In most mammals including man, Q10 predominates.

Coenzyme Q10 is particularly advantageous and is characterized by the following structural formula:

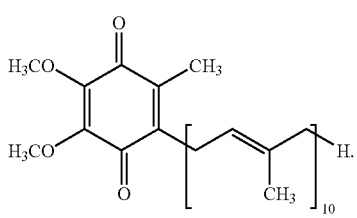

Plastoquinones have the general structural formula

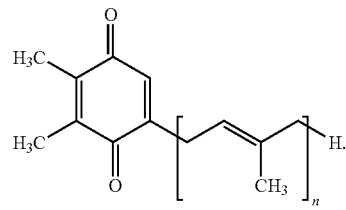

Plastoquinones differ in the number n of isoprene radicals and are referred to accordingly, e.g. PQ-9 (n=9). In addition, other plastoquinones with varying substituents on the quinone ring exist.

Creatine and/or creatine derivatives are preferred active ingredients for the purposes of the present invention. Creatine is characterized by the following structure:

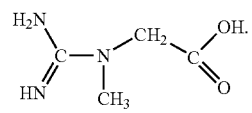

Preferred derivatives are creatine phosphate and creatine sulfate, creatine acetate, creatine ascorbate and the derivatives esterified at the carboxyl group with mono- or polyfunctional alcohols.

A further advantageous active ingredient is L-carnitine [3-hydroxy-4-(trimethylammonio)butyrobetaine]. Acylcarnitine which chosen from the group of substances of the following general structural formula

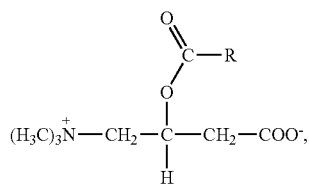

where R is chosen from the group of branched and unbranched alkyl radicals having up to 10 carbon atoms, are advantageous active ingredients for the purposes of the present invention. Preference is given to propionylcarnitine and, in particular, acetylcarnitine. Both enantiomers (D and L form) are to be used advantageously for the purposes of the present invention. It may also be advantageous to use any enantiomer mixtures, for example a racemate of D and L form.

Further advantageous active ingredients are sericoside, pyridoxol, vitamin K and biotin and aroma substances.

The list of said active ingredients and active ingredient combinations which can be used in the impregnation solutions according to the invention is, of course, not intended to be limiting. The active ingredients can be used individually or in any combinations with one another.

Cosmetic and dermatological impregnation solutions in the form of a sunscreen are favorable. It is, however, also advantageous for the purposes of the present inventions to provide cosmetic and dermatological cloths whose main use purpose is not protection against sunlight, but which nevertheless contain a content of UV protection substances.

UV protection substances, like antioxidants, and, if desired, preservatives, also provide effective protection of the impregnation solutions themselves against spoilage.

Accordingly, for the purposes of the present invention, the impregnation solutions preferably comprise at least one UV-A and/or UV-B filter substance. The formulations may, although not necessarily, optionally also comprise one or more organic and/or inorganic pigments as UV filter substances which may be present in the water and/or oil phase.

Preferred inorganic pigments are metal oxides and/or other metal compounds which are insoluble or virtually insoluble in water, in particular oxides of titanium ($TiO_2$), zinc (ZnO), iron (e.g. $Fe_2O_3$), zirconium ($ZrO_2$), silicon ($SiO_2$), manganese (e.g. MnO), aluminum ($Al_2O_3$), cerium (e.g. $Ce_2O_3$), mixed oxides of the corresponding metals and mixtures of such oxides.

For the purposes of the present invention, such pigments may advantageously be surface-treated ("coated"), the intention being to form or retain, for example, an amphiphilic or hydrophobic character. This surface treatment can consist in providing the pigments with a thin hydrophobic layer by processes known per se.

Advantageous according to the invention are e.g. titanium dioxide pigments which have been coated with octylsilanol. Suitable titanium dioxide particles are available under the trade name T805 from Degussa. Also particularly advantageous are $TiO_2$ pigments coated with aluminum stearate, e.g. those available under the trade name MT 100 T from TAYCA.

A further advantageous coating of the inorganic pigments consists of dimethylpolysiloxane (also: dimethicone), a mixture of completely methylated, linear siloxane polymers which have been terminally blocked with trimethylsiloxy units. Particularly advantageous for the purposes of the present invention are zinc oxide pigments coated in this way.

Also advantageous is a coating of the inorganic pigments with a mixture of dimethylpolysiloxane, in particular dimethylpolysiloxane having an average chain length of from 200 to 350 dimethylsiloxane units, and silica gel, which is also referred to as simethicones. In particular, it is advantageous for the inorganic pigments to be additionally coated with aluminum hydroxide or aluminum oxide hydrate (also: alumina, CAS No.: 1333-84-2). Particularly advantageous are titanium dioxides which have been coated with simethicones and alumina, it also being possible for the coating to comprise water. An example thereof is the titanium dioxide available under the trade name Eusolex T2000 from Merck.

An advantageous organic pigment for the purposes of the present invention is 2,2'-methylenebis(6-(2H-benzotriazol-2-yl)-4-(1,1,3,3-tetramethylbutyl)phenol) [INCI:bisoctyltriazole], which is characterized by the chemical structural formula

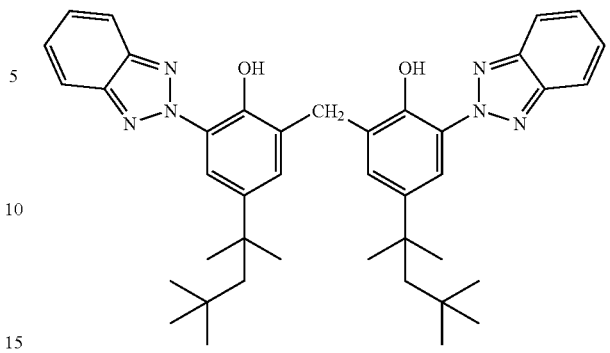

and is available under the trade name Tinosorb® M from CIBA-Chemikalien GmbH.

Impregnation solutions according to the invention advantageously comprise substances which absorb UV irradiation in the UV-A and/or UV-B region, the total amount of filter substances being, for example, 0.1% by weight to 30% by weight, preferably 0.5 to 20% by weight, in particular 1.0 to 15.0% by weight, based on the total weight of the impregnation solutions, in order to make available cosmetic impregnation solutions which protect the hair or the skin from the entire range of ultraviolet radiation. They can also be used as sunscreens for hair or skin.

Advantageous UV-A filter substances for the purposes of the present invention are dibenzoylmethane derivatives, in particular 4-(tert-butyl)4'-methoxydibenzoylmethane (CAS No. 70356-09-1), which is sold by Givaudan under the trade name Parsol® 1789 and by Merck under the trade name Eusolex® 9020.

Further advantageous UV-A filter substances are phenylene-1,4-bis(2-benzimidazyl)-3,3'-5,5'-tetrasulfonic acid and its salts, particularly the corresponding sodium, potassium or triethanolammonium salts, in particular the phenylene-1,4-bis(2-benzimidazyl)-3,3'-5,5'-tetrasulfonic acid bis-sodium salt with the INCI name bisimidazylates, which is available, for example, under the trade name Neo Heliopan AP from Haarmann & Reimer, and 1,4-di(2-oxo-10-sulfo-3-bornylidenemethyl)benzene and salts thereof (in particular the corresponding 10-sulfato compounds, in particular the corresponding sodium, potassium or triethanolammonium salt), which is also referred to as benzene-1,4-di(2-oxo-3-bornylidenemethyl-10-sulfonic acid).

Advantageous UV filter substances for the purposes of the present invention are also "broad-band filters", i.e. filter substances which absorb both UV-A and also UV-B radiation.

Advantageous broad-band filters or UV-B filter substances are, for example, bisresorcinyltriazine derivatives. Particularly preferred are 2,4-bis{[4-(2-ethylhexyloxy)-2-hydroxy]phenyl}-6-(4-methoxyphenyl)-1,3,5-triazine (INCI: Aniso Triazine), which is available under the trade name Tinosorb® S from CIBA-Chemikalien GmbH, and 4,4',4"-(1,3,5-triazine-2,4,6-triyltriimino)trisbenzoic acid tris(2-ethylhexyl ester), synonym: 2,4,6-tris[anilino(p-carbo-2'-ethyl-1'-hexyloxy)]-1,3,5-triazine (INCI: Octyl Triazone), which is sold by BASF Aktiengesellschaft under the trade name UVINUL® T 150.

A particularly preferred UV filter substance for the purposes of the present invention is also an asymmetrically substituted s-triazine which is also referred to as dioctylbutylamidotriazone (INCI: dioctylbutamidotriazone) and is available under the trade name UVA-SORB HEB from Sigma 3V.

Also advantageous for the purposes of the present invention are 2,4-bis{[4-(3-sulfonato)2-hydroxypropyloxy)-2-hydroxy]phenyl}-6-(4-methoxyphenyl)-1,3,5-triazine sodium salt, 2,4-bis{[4-(3-(2-propyloxy)-2-hydroxypropyloxy)-2-hydroxy]phenyl}-6-(4-methoxyphenyl)-1,3,5-triazine, 2,4-bis{[4-(2-ethylhexyloxy)-2-hydroxy]phenyl}-6-[4-(2-methoxyethylcarboxyl)phenylamino]-1,3,5-triazine, 2,4-bis{[4-(3-(2-propyloxy)-2-hydroxy-propyloxy)-2-hydroxy]phenyl}-6-[4-(2-ethylcarboxyl)phenylamino]-1,3,5-triazine, 2,4-bis{[4-(2-ethylhexyloxy)-2-hydroxy]phenyl}-6-(1-methylpyrrol-2-yl)-1,3,5-triazine, 2,4-bis{[4-tris(trimethylsiloxysilyl propyloxy)-2-hydroxy]phenyl}-6-(4-methoxyphenyl)-1,3,5-triazine, 2,4-bis{[4-(2"-methylpropenyloxy)-2-hydroxy]phenyl}-6-(4-methoxyphenyl)-1,3,5-triazine and 2,4-bis{[4-(1',1',1',3',5',5',5'-heptamethylsiloxy-2"-methylpropyloxy)-2-hydroxy]phenyl}-6-(4-methoxyphenyl)-1,3,5-triazine.

An advantageous broadband filter for the purposes of the present invention is 2,2'-methylenebis(6-(2H-benzotriazol-2-yl)-4-(1,1,3,3-tetramethylbutyl)phenol), which is available under the trade name Tinosorb® M from CIBA-Chemikalien GmbH.

An advantageous broadband filter for the purposes of the present invention is also 2-(2H-benzotriazol-2-yl)-4-methyl-6-[2-methyl-3-[1,3,3,3-tetramethyl-1-[(trimethylsilyl)oxy]disiloxanyl]propyl]phenol (CAS No.: 155633-54-8) with the INCI name Drometrizole trisiloxane.

The UV-B filters may be oil-soluble or water-soluble. Advantageous oil-soluble UV-B filter substances are e.g.:

3-benzylidenecamphor derivatives, preferably 3-(4-methylbenzylidene)camphor, 3-benzylidenecamphor;

4-aminobenzoic acid derivatives, preferably 2-ethylhexyl 4-(dimethylamino)benzoate, amyl 4-(dimethylamino)benzoate;

2,4,6-trianilino-(p-carbo-2'-ethyl-1'-hexyloxy)-1,3,5-triazine;

esters of benzalmalonic acid, preferably di(2-ethylhexyl) 4-methoxybenzalmalonate;

esters of cinnamic acid, preferably 2-ethylhexyl 4-methoxycinnamate, isopentyl 4-methoxycinnamate;

derivatives of benzophenone, preferably 2-hydroxy-4-methoxybenzophenone, 2-hydroxy-4-methoxy-4'-methylbenzophenone, 2,2'-dihydroxy-4-methoxybenzophenone and UV filters bonded to polymers.

Advantageous water-soluble UV-B filter substances are e.g.:

salts of 2-phenylbenzimidazole-5-sulfonic acid, such as its sodium, potassium or its triethanolammonium salt, and the sulfonic acid itself;

sulfonic acid derivatives of 3-benzylidenecamphor, such as e.g. 4-(2-oxo-3-bornylidenemethyl)benzenesulfonic acid, 2-methyl-5-(2-oxo-3-bornylidenemethyl)sulfonic acid and salts thereof.

A further light protection filter substance to be used advantageously according to the invention is ethylhexyl 2-cyano-3,3-diphenylacrylate (octocrylene), which is available from BASF under the trade name Uvinul® N 539.

It may also be of considerable advantage to use polymer-bonded or polymeric UV filter substances in impregnation solutions according to the present invention, particularly those described in WO-A-92/20690.

In some instances, it may also be advantageous to incorporate further UV-A and/or UV-B filters according to the invention into the cosmetic or dermatological impregnation solutions, for example certain salicylic acid derivatives, such as 4-isopropylbenzyl salicylate, 2-ethylhexyl salicylate (=octyl salicylate), homomenthyl salicylate.

The list of said UV filters which can be used for the purposes of the present invention is not of course intended to be limiting.

The cosmetic and dermatological cloths according to the invention can also advantageously comprise dyes and/or color pigments, particularly if they are to be used in the decorative cosmetics sector. The dyes and pigments can be chosen from the corresponding positive list of the Cosmetics Directive or the EC list of cosmetic colorants. In most cases they are identical to the dyes approved for foods. Advantageous color pigments are, for example, titanium dioxide, mica, iron oxides (e.g. $Fe_2O_3$, $Fe_3O_4$, FeO(OH)) and/or zinc oxide. Advantageous dyes are, for example, carmine, Berlin blue, chrome oxide green, ultramarine blue and/or manganese violet. It is particularly advantageous to choose the dyes and/or color pigments from the following list. The Colour Index Numbers (CIN) are taken from the *Rowe Colour Index, 3rd Edition, Society of Dyers and Colourists*, Bradford, England, 1971.

| Chemical or other name | CIN | Color |
| --- | --- | --- |
| Pigment Green | 10006 | green |
| Acid Green 1 | 10020 | green |
| 2,4-Dinitrohydroxynaphthalene-7-sulfonic acid | 10316 | yellow |
| Pigment Yellow 1 | 11680 | yellow |
| Pigment Yellow 3 | 11710 | yellow |
| Pigment Orange 1 | 11725 | orange |
| 2,4-Dihydroxyazobenzene | 11920 | orange |
| Solvent Red 3 | 12010 | red |
| 1-(2'-Chloro-4'-nitro-1'-phenylazo)-2-hydroxynaphthalene | 12085 | red |
| Pigment Red 3 | 12120 | red |
| Ceres red; Sudan red; Fat Red G | 12150 | red |
| Pigment Red 112 | 12370 | red |
| Pigment Red 7 | 12420 | red |
| Pigment Brown 1 | 12480 | brown |
| 4-(2'-Methoxy-5'-sulfodiethylamido-1'-phenylazo)-3-hydroxy-5"-chloro-2",4"-dimethoxy-2-naphthanilide | 12490 | red |
| Disperse Yellow 16 | 12700 | yellow |
| 1-(4-Sulfo-1-phenylazo)-4-aminobenzene-5-sulfonic acid | 13015 | yellow |
| 2,4-Dihydroxyazobenzene-4'-sulfonic acid | 14270 | orange |
| 2-(2,4-Dimethylphenylazo-5-sulfo)-1-hydroxynaphthalene-4-sulfonic acid | 14700 | red |
| 2-(4-Sulfo-1-naphthylazo)-1-naphthol-4-sulfonic acid | 14720 | red |
| 2-(6-Sulfo-2,4-xylylazo)-1-naphthol-5-sulfonic acid | 14815 | red |
| 1-(4'-Sulfophenylazo)-2-hydroxynaphthalene | 15510 | orange |
| 1-(2-Sulfo-4-chloro-5-carboxy-1-phenylazo)-2-hydroxynaphthalene | 15525 | red |
| 1-(3-Methylphenylazo-4-sulfo)-2-hydroxynaphthalene | 15580 | red |
| 1-(4',(8')-Sulfonaphthylazo)-2-hydroxynaphthalene | 15620 | red |
| 2-Hydroxy-1,2'-azonaphthalene-1'-sulfonic acid | 15630 | red |
| 3-Hydroxy-4-phenylazo-2-naphthylcarboxylic acid | 15800 | red |
| 1-(2-Sulfo-4-methyl-1-phenylazo)-2-naphthylcarboxylic acid | 15850 | red |
| 1-(2-Sulfo-4-methyl-5-chloro-1-phenylazo)-2-hydroxynaphthalene-3-carboxylic acid | 15865 | red |
| 1-(2-Sulfo-1-naphthylazo)-2-hydroxynaphthalene-3-carboxylic acid | 15880 | red |
| 1-(3-Sulfo-1-phenylazo)-2-naphthol-6-sulfonic acid | 15980 | orange |

-continued

| Chemical or other name | CIN | Color |
| --- | --- | --- |
| 1-(4-Sulfo-1-phenylazo)-2-naphthol-6-sulfonic acid | 15985 | yellow |
| Allura Red | 16035 | red |
| 1-(4-Sulfo-1-naphthylazo)-2-naphthol-3,6-disulfonic acid | 16185 | red |
| Acid Orange 10 | 16230 | orange |
| 1-(4-Sulfo-1-naphthylazo)-2-naphthol-6,8-disulfonic acid | 16255 | red |
| 1-(4-Sulfo-1-naphthylazo)-2-naphthol-3,6,8-trisulfonic acid | 16290 | red |
| 8-Amino-2-phenylazo-1-naphthol-3,6-disulfonic acid | 17200 | red |
| Acid Red 1 | 18050 | red |
| Acid Red 155 | 18130 | red |
| Acid Yellow 121 | 18690 | yellow |
| Acid Red 180 | 18736 | red |
| Acid Yellow 11 | 18820 | yellow |
| Acid Yellow 17 | 18965 | yellow |
| 4-(4-Sulfo-1-phenylazo)-1-(4-sulfophenyl)-5-hydroxy-pyrazolone-3-carboxylic acid | 19140 | yellow |
| Pigment Yellow 16 | 20040 | yellow |
| 2,6-(4'-Sulfo-2'',4''-dimethyl)bisphenylazo)1,3-dihydroxybenzene | 20170 | orange |
| Acid Black 1 | 20470 | black |
| Pigment Yellow 13 | 21100 | yellow |
| Pigment Yellow 83 | 21108 | yellow |
| Solvent Yellow | 21230 | yellow |
| Acid Red 163 | 24790 | red |
| Acid Red 73 | 27290 | red |
| 2-[4'-(4''-Sulfo-1''-phenylazo)-7'-sulfo-1'-naphthylazo]-1-hydroxy-7-aminonaphthalene-3,6-disulfonic acid | 27755 | black |
| 4'-[(4''-Sulfo-1''-phenylazo)-7'-sulfo-1'-naphthylazo]-1-hydroxy-8-acetylaminonaphthalene-3,5-disulfonic acid | 28440 | black |
| Direct Orange 34, 39, 44, 46, 60 | 40215 | orange |
| Food Yellow | 40800 | orange |
| trans-β-Apo-8'-carotinaldehyde (C30) | 40820 | orange |
| trans-Apo-8'-carotinic acid (C30)-ethyl ester | 40825 | orange |
| Canthaxanthin | 40850 | orange |
| Acid Blue 1 | 42045 | blue |
| 2,4-Disulfo-5-hydroxy-4'-4''-bis(diethylamino)triphenylcarbinol | 42051 | blue |
| 4-[(-4-N-Ethyl-p-sulfobenzylamino)phenyl(4-hydroxy-2-sulfophenyl)(methylene)-1-(N-ethyl,N-p-sulfobenzyl)-2,5-cyclohexadienimine] | 42053 | green |
| Acid Blue 7 | 42080 | blue |
| (N-Ethyl-p-sulfobenzylamino)phenyl(2-sulfophenyl)methylene-(N-ethyl-N-p-sulfobenzyl)$\Delta^{2,5}$-cyclohexadienimine | 42090 | blue |
| Acid Green 9 | 42100 | green |
| Diethyldisulfobenzyldi-4-amino-2-chloro-di-2-methyl-fuchsonimmonium | 42170 | green |
| Basic Violet 14 | 42510 | violet |
| Basic Violet 2 | 42520 | violet |
| 2'-Methyl-4'-(N-ethyl-N-m-sulfobenzyl)amino-4''-(N-diethyl)amino-2-methyl-N-ethylN-m-sulfobenzylfuchsonimmonium | 42735 | blue |
| 4'-(N-Dimethyl)amino-4''-(N-phenyl)aminonaphtho-N-dimethyl-fuchsonimmonium | 44045 | blue |
| 2-Hydroxy-3,6-disulfo-4,4'-bisdimethylaminonaphtho-fuchsonimmonium | 44090 | green |
| Acid Red 52 | 45100 | red |
| 3-(2'-Methylphenylamino)-6-(2'-methyl-4'-sulfophenylamino)-9-(2''-carboxyphenyl)xanthenium salt | 45190 | violet |
| Acid Red 50 | 45220 | red |
| Phenyl-2-oxyfluorone-2-carboxylic acid | 45350 | yellow |
| 4,5-Dibromofluorescein | 45370 | orange |
| 2,4,5,7-Tetrabromofluorescein | 45380 | red |
| Solvent Dye | 45396 | orange |
| Acid Red 98 | 45405 | red |
| 3',4',5',6'-Tetrachloro-2,4,5,7-tetrabromofluorescein | 45410 | red |
| 4,5-Diiodofluorescein | 45425 | red |
| 2,4,5,7-Tetraiodofluorescein | 45430 | red |
| Quinophthalone | 47000 | yellow |
| Quinophthalonedisulfonic acid | 47005 | yellow |
| Acid Violet 50 | 50325 | violet |
| Acid Black 2 | 50420 | black |
| Pigment Violet 23 | 51319 | violet |
| 1,2-Dioxyanthraquinone, calcium-aluminum complex | 58000 | red |
| 3-Oxypyrene-5,8,10-sulfonic acid | 59040 | green |
| 1-Hydroxy-4-N-phenylaminoanthraquinone | 60724 | violet |
| 1-Hydroxy-4-(4'-methylphenylamino)anthraquinone | 60725 | violet |
| Acid Violet 23 | 60730 | violet |
| 1,4-Di(4'-methylphenylamino)anthraquinone | 61565 | green |
| 1,4-Bis(o-sulfo-p-toluidino)anthraquinone | 61570 | green |
| Acid Blue 80 | 61585 | blue |
| Acid Blue 62 | 62045 | blue |
| N,N'-Dihydro-1,2,1',2'-anthraquinone azine | 69800 | blue |
| Vat Blue 6; Pigment Blue 64 | 69825 | blue |
| Vat Orange 7 | 71105 | orange |
| Indigo | 73000 | blue |
| Indigo-disulfonic acid | 73015 | blue |
| 4,4'-Dimethyl-6,6'-dichlorothioindigo | 73360 | red |
| 5,5'-Dichloro-7,7'-dimethylthioindigo | 73385 | violet |
| Quinacridone Violet 19 | 73900 | violet |
| Pigment Red 122 | 73915 | red |
| Pigment Blue 16 | 74100 | blue |
| Phthalocyanine | 74160 | blue |
| Direct Blue 86 | 74180 | blue |
| Chlorinated phthalocyanine | 74260 | green |
| Natural Yellow 6, 19; Natural Red 1 | 75100 | yellow |
| Bixin, Norbixin | 75120 | orange |
| Lycopene | 75125 | yellow |
| trans-alpha-, beta- and gamma-carotene | 75130 | orange |
| Keto- and/or hydroxyl derivates of carotene | 75135 | yellow |
| Guanine or pearlizing agent | 75170 | white |
| 1,7-Bis(4-hydroxy-3-methoxyphenyl)1,6-heptadiene-3,5-dione | 75300 | yellow |
| Complex salt (Na, Al, Ca) of carminic acid | 75470 | red |
| Chlorophyll a and b; copper compounds of chlorophylls and Chlorophyllins | 75810 | green |
| Aluminum | 77000 | white |
| Hydrated alumina | 77002 | white |
| Hydrous aluminum silicates | 77004 | white |
| Ultramarine | 77007 | blue |
| Pigment Red 101 and 102 | 77015 | red |
| Barium sulfate | 77120 | white |
| Bismuth oxychloride and its mixtures with mica | 77163 | white |
| Calcium carbonate | 77220 | white |
| Calcium sulfate | 77231 | white |
| Carbon | 77266 | black |
| Pigment black 9 | 77267 | black |
| Carbo medicinalis vegetabilis | 77268:1 | black |
| Chromium oxide | 77288 | green |
| Chromium oxide, hydrous | 77289 | green |
| Pigment Blue 28, Pigment Green 14 | 77346 | green |
| Pigment Metal 2 | 77400 | brown |
| Gold | 77480 | brown |
| Iron oxides and hydroxides | 77489 | orange |
| Iron oxide | 77491 | red |
| Iron oxide, hydrated | 77492 | yellow |
| Iron oxide | 77499 | black |
| Mixtures of iron (II) and iron(III) hexacyanoferrate | 77510 | blue |
| Pigment White 18 | 77713 | white |
| Manganese animonium diphosphate | 77742 | violet |
| Manganese phosphate; $Mn_3(PO_4)_2 \cdot 7 H_2O$ | 77745 | red |
| Silver | 77820 | white |
| Titanium dioxide and its mixtures with mica | 77891 | white |
| Zinc oxide | 77947 | white |
| 6,7-Dimethyl-9-(1'-D-ribityl)isoalloxazine, lactoflavine | | yellow |
| Sugar colouring | | brown |
| Capsanthin, capsorubin | | orange |
| Betanin | | red |
| Benzopyrylium salts, Anthocyans | | red |
| Aluminum, zinc, magnesium and calcium stearate | | white |

-continued

| Chemical or other name | CIN | Color |
|---|---|---|
| Bromothymol blue | | blue |
| Bromocresol green | | green |
| Acid Red 195 | | red |

If the cloths according to the invention are intended for use in the facial area, it is favorable to choose one or more substances from the following group as the dye: 2,4-dihydroxyazobenzene, 1-(2'-chloro4'-nitro-1'-phenylazo)-2-hydroxynaphthalene, Ceres Red, 2-(4-sulfo-1-naphthylazo)-1-naphthol-4-sulfonic acid, calcium salt of 2-hydroxy-1,2'-azonaphthalene-1'-sulfonic acid, calcium and barium salts of 1-(2-sulfo-4-methyl-1-phenylazo)-2-naphthylcarboxylic acid, calcium salt of 1-(2-sulfo-1-naphthylazo)-2-hydroxynaphthalene-3-carboxylic acid, aluminum salt of 1-(4-sulfo-1-phenylazo)-2-naphthol-6-sulfonic acid, aluminum salt of 1-(4-sulfo-1-naphthylazo)-2-naphthol-3,6-disulfonic acid, 1-(4-sulfo-1-naphthylazo)-2-naphthol-6,8-disulfonic acid, aluminum salt of 4-(4-sulfo-1-phenylazo)-1-(4-sulfophenyl)-5-hydroxypyrazolone-3-carboxylic acid, aluminum and zirconium salts of 4,5-dibromofluorescein, aluminum and zirconium salts of 2,4,5,7-tetrabromofluorescein, 3',4',5',6'-tetrachloro-2,4,5,7-tetrabromofluorescein and its aluminum salt, aluminum salt of 2,4,5,7-tetraiodofluorescein, aluminum salt of quinophthalone disulfonic acid, aluminum salt of indigo disulfonic acid, red and black iron oxide (CIN: 77 491 (red) and 77 499 (black)), iron oxide hydrate (CIN: 77 492), manganese ammonium diphosphate and titanium dioxide.

Also advantageous are oil-soluble natural dyes, such as, for example, paprika extracts, β-carotene or cochenille.

Also advantageous for the purposes of the present invention are impregnated cloths with a content of pearlescent pigments. Preference is given in particular to the types of pearlescent pigments listed below:

1. Natural pearlescent pigments, such as, for example "pearl essence" (guanine/hypoxanthin mixed crystals from fish scales) and
   "mother of pearl" (ground mussel shells)
2. Monocrystalline pearlescent pigments, such as, for example, bismuth oxychloride (BiOCl)
3. Layer substrate pigments: e.g. mica/metal oxide Bases for pearlescent pigments are, for example, pulverulent pigments or castor oil dispersions of bismuth oxychloride and/or titanium dioxide, and bismuth oxichloride and/or titanium dioxide on mica. The luster pigment listed under CIN 77163, for example, is particularly advantageous.

Also advantageous are, for example, the following types of pearlescent pigment based on mica/metal oxide:

| Group | Coating/layer | Color |
|---|---|---|
| Silver-white pearlescent | TiO$_2$: 40-60 nm | silver |
| Interference pigments | TiO$_2$: 60-80 nm | yellow |
| | TiO$_2$: 80-100 nm | red |
| | TiO$_2$: 100-140 nm | blue |
| | TiO$_2$: 120-160 nm | green |
| Color luster pigments | Fe$_2$O$_3$ | bronze |
| | Fe$_2$O$_3$ | copper |
| | Fe$_2$O$_3$ | Red |
| | Fe$_2$O$_3$ | Red-violet |
| | Fe$_2$O$_3$ | Red-green |
| | Fe$_2$O$_3$ | Black |
| Combination pigments | TiO$_2$/Fe$_2$O$_3$ | Gold shades |
| | TiO$_2$/Cr$_2$O$_3$ | Green |
| | TiO$_2$/Berlin blue | deep blue |
| | TiO$_2$/carmine | red |

Particular preference is given, for example, to the pearlescent pigments obtainable from Merck under the trade names Timiron, Colorona or Dichrona.

The list of given pearlescent pigments is not of course intended to be limiting. Pearlescent pigments which are advantageous for the purposes of the present invention are obtainable by numerous methods known per se. For example, other substrates apart from mica can be coated with further metal oxides, such as, for example, silica and the like. SiO$_2$ particles coated with, for example, TiO$_2$ and Fe$_2$O$_3$ ("ronaspheres"), which are marketed by Merck and are particularly suitable for the optical reduction of fine lines.

It can moreover be advantageous to dispense completely with a substrate such as mica. Particular preference is given to iron pearlescent pigments prepared without the use of mica. Such pigments are obtainable, for example, under the trade name Sicopearl Kupfer 1000 from BASF.

In addition, also particularly advantageous are effect pigments which are available under the trade name Metasome Standard/Glitter in various colors (yellow, red, green, blue) from Flora Tech. The glitter particles are present here in the mixtures with various auxiliaries and dyes (such as, for example, the dyes with the Colour Index (CI) Numbers 19140, 77007, 77289, 77491).

The dyes and pigments may be present either individually or in a mixture, and can be mutually coated with one another, different coating thicknesses generally giving rise to different color effects. The total amount of dyes and color-imparting pigments is advantageously chosen from the range from e.g. 0.1% by weight to 30% by weight, preferably from 0.5 to 15% by weight, in particular from 1.0 to 10% by weight, in each case based on the total weight of the impregnation solutions.

Also advantageous for the purposes of the present invention are cloths which are used as cosmetic or dermatological deodorant or antiperspirant cloths.

According to the invention, the cloths particularly advantageously comprise one or more of the customary deodorizing and/or antiperspirant active ingredients, for example odor maskers, such as the customary perfume constituents, odor absorbers, for example the phyllosilicates described in the patent laid-open specification DE-P 40 09 347, and of these in particular montmorillonite, kaolinite, nontronite, saponite, hectorite, bentonite, smectite, and furthermore, for example, zinc salts of ricinoleic acid. Germicidal agents are also suitable for incorporation into the impregnation solutions according to the invention. Advantageous substances are 2,4,4'-trichloro-2'hydroxydiphenyl ether (Irgasan), 1,6-di(4-chlorophenylbiguanido)hexane (chlorhexidine), 3,4,4'-trichlorocarbanilide, quaternary ammonium compounds, oil of cloves, mint oil, thyme oil, triethyl citrate, farnesol (3,7,11-trimethyl-2,6,10-dodecatrien-1-ol), and the active agents described in the patent laid-open specifications DE-3740 186, DE-39 38 140, DE-42 04321, DE42 29707, DE-42 29737, DE-42 37081, DE-43 09 372, DE-43 24 219.

The customary antiperspirant active ingredients can likewise advantageously be used, for example, aluminum chloride, aluminum chlorhydrate, nitrate, sulfate, acetate etc. In addition, also advantageous are zinc, magnesium and zirconium compounds. Customary antiperspirant active ingredients which can preferably be used are, for example, described in: H. P. Fiedler, Der Schweiβ, Editio Cantor, Aulendorf, 2nd Edition, pp. 303-377, Chapter K: *"Mittel zur Hemmung der Transpiration"* [Agents for inhibiting perspiration].

It is also advantageous for the purposes of the present invention to provide cosmetic and dermatological cloths whose main purpose is not the deodorizing or antiperspirant action, but which nevertheless have a content of customary deodorizing and/or antiperspirant active ingredients.

The cloths according to the invention are also highly suitable as carriers for dermatological active ingredients, e.g. as carriers for substances effective against acne. Acne is a skin disorder with many forms and causes, characterized by non-inflamed and inflamed bumps, originating from blocked hair follicles (comedones) which can lead to the formation of pustules, abscesses and scars. The most frequent is Acne vulgaris which occurs predominantly in puberty. Causative conditions for Acne vulgaris are the keratinization and blocking of the hair follicle opening, the production of sebum, which is dependent on the level of male sex hormones in the blood, and the production of free fatty acids and tissue-damaging enzymes by bacteria (*propionibacterium acnes*).

It is therefore advantageous to add to the impregnation solutions according to the invention substances which are effective against acne, which are effective, for example, against *propionibactedum acnes* (for example those described in DE-A 42 29 707, DE-A 43 05 069, DE-A 43 07 976, DE-A 43 37 71 1, DE-A 43 29 379), but also other substances effective against acne, for example all-trans-retinoic acid, 13-cis-retinoic acid and related substances) or antiinflammatory active ingredients, for example batyl alcohol (α-octadecyl glyceryl ether), selachyl alcohol (α-9-octadecenyl glyceryl ether), chimyl alcohol (α-hexadecyl glyceryl ether) and/or bisabolol, and antibiotics and/or keratolytics.

Keratolytics are substances which soften keratinized skin (such as, for example, warts, corns, calouses and the like) so that it can be removed more easily or so that it falls off or peels off.

All common substances effective against acne can be used advantageously, in particular benzoyl peroxide, bituminosulfonates (ammonium, sodium and calcium salts of shale oil sulfonic acids), salicylic acid (2-hydroxybenzoic acid), miconazole (1-[2-(2,4-dichlorobenzyloxy)-2-(2,4-dichlorophenyl)ethyl]imidazole) and derivatives, adapalene (6-[3-(1-adamantyl)4-methoxyphenyl]-2-naphthoic acid), azaleic acid (nonanedioc acid), mesulfene (2,7-dimethylthianthrene, $C_{14}H_{12}S_2$), and aluminum oxide, zinc oxide and/or finely divided sulfur.

The amount of antiacne agents (one or more compounds) in the impregnation solutions is preferably 0.01 to 30% by weight, particularly preferably 0.1 to 20% by weight, in particular 1 to 10% by weight, based on the total weight of the impregnation solution.

According to the invention, "dry" cloths are preferably used in combination with the low-viscosity cosmetic and dermatological impregnation solutions, which cloths consist of nonwoven, in particular of water-jet-consolidated and/or water-jet-impressed nonwoven.

Nonwovens of this kind may have macroimpressions of any desired pattern. The choice to be made depends, firstly, on the impregnation to be applied and, secondly, on the later intended use for the cloth.

If embossed nonwovens are used, the large cavities on the nonwoven surface and within the nonwoven facilitate the uptake of soiling and contaminations when the impregnated cloth is passed over the skin. The cleaning action may be increased many times over relative to the unembossed cloths.

It has proven advantageous for the cloth to have a weight of 35 to 120 $g/m^2$, preferably from 40 to 60 $g/m^2$ (measured at 20° C.±2° C. and at a humidity of the room air of 65%±5% for 24 hours).

The thickness of the nonwoven is preferably 0.4 mm to 2 mm, in particular 0.6 mm to 0.9 mm.

Starting materials for the nonwoven material of the cloth which can be used are generally all organic and inorganic natural and synthetic based fiber materials. Examples which may be given are viscose, cotton, cellulose, jute, hemp, sisal, silk, wool, polypropylene, polyester, polyethylene terephthalate (PET), aramid, nylon, polyvinyl derivatives, polyurethanes, polylactide, polyhydroxyalkanoate, cellulose esters and/or polyethylene and also mineral fibers, such as glass fibers or carbon fibers. However, the present invention is not limited to said materials, it being possible to use a large number of further fibers for forming the nonwoven. It is particularly advantageous in the sense of the present invention for the fibers used to be water-insoluble.

In a particularly advantageous embodiment of the nonwoven, the fibers consist of a mixture of 70% of viscose and 30% of PET.

Also particularly advantageous are fibers of high-strength polymers, such as polyamide, polyesters and/or highly drawn polyethylene.

Moreover, the fibers can also be colored in order to be able to emphasize and/or increase the optical attractiveness of the nonwoven. The fibers may additionally comprise UV stabilizers and/or preservatives.

The fibers used to form the cloth preferably have a water-absorption rate of more than 60 mm/[10 min] (measured using the EDANA Test 10.1-72), in particular more than 80 mm/[10 min].

In addition, the fibers used to form the cloth preferably have a water-absorption capacity of more than 5 g/g (measured using the EDANA Test 10.1-72), in particular more than 8 g/g. 10 Advantageous wipes in the sense of the present invention have a tear strength of, in particular

|  |  | [N/50 mm] |
| --- | --- | --- |
| In the dry state | Machine direction | >60, preferably >80 |
|  | Cross direction | >20, preferably >30 |
| In the impregnated | Machine direction | >4, preferably >60 |
| state | Cross direction | >10, preferably >20 |

The expandability of the advantageous cloth is preferably

| In the dry state | Machine direction | 15% to 100%, preferably 20% and 50% |
| --- | --- | --- |
|  | Cross direction | 40% to 120%, preferably 50% and 85% |
| In the impregnated | Machine direction | 15% to 100%, preferably 20% and 40% |
| state | Cross direction | 40% to 120%, preferably 50% and 85% |

The examples below serve to illustrate the impregnation solutions according to the invention without limiting them.

The numerical values in the examples are percentages by weight, based on the total weight of the respective impregnation solutions.

EXAMPLES

Impregnation solution 1: Aftersun/skincare microemulsion

| Constituent | Amount/% by weight |
|---|---|
| Glyceryl stearate citrate | 2 |
| Cetyl alcohol | 1 |
| Dicaprylyl carbonate | 5 |
| Octyldodecanol | 3 |
| Cylomethicone | 1 |
| Butylene glycol | 3 |
| Ethanol | 5 |
| DMDM hydantoin | 0.6 |
| Octoxyglycerol | 1 |
| Antioxidants | 0.5 |
| Perfume | 0.5 |
| Dyes | 0.3 |
| Water | ad 100 |

Impregnation solution 2: Nongreasy bodycare emulsion

| Constituent | % by weight |
|---|---|
| Glyceryl stearate citrate | 3.5 |
| Cetyl palmitate | 3 |
| Dicaprylyl ether | 5 |
| Cycolmethicone | 3 |
| Phenyltrimethicone | 1 |
| Paraffin wax | 2 |
| Glycerol | 7.5 |
| Parabens | 1 |
| Phenoxyethanol | 1 |
| AGR | 0.5 |
| Perfume | 0.5 |
| Dyes | 0.5 |
| Water | ad 100 |

Impregnation solution 3: Sunscreen for a silky feel on the skin

| Constituent | % by weight |
|---|---|
| Glyceryl stearate citrate | 4 |
| Stearyl alcohol | 3 |
| Dicaprylyl ether | 5 |
| Octyldodecanol | 3 |
| Phenyltrimethicone | 1 |
| Bisethylhexyloxyphenol methoxyphenyl triazine | 2 |
| Octocrylene | 7 |
| Diethylhexyl butamidotriazone | 1 |
| Ethylhexyl methoxycinnamate | 4 |
| Butylene glycol | 1 |
| Vitamin E acetate | 1 |
| PVP/hexadecene copolymer | 1 |
| Parabens | 1 |
| Antioxidants | 0.5 |
| Perfume | 0.5 |
| Water | ad 100 |

Impregnation solution 4: Sunscreen formulation

| Constituent | % by weight |
|---|---|
| Glyceryl stearate citrate | 2 |
| Stearyl alcohol | 1 |
| Dicaprylyl carbonate | 5 |
| Octyldodecanol | 3 |
| $C_{12-15}$ alkyl benzoate | 1 |
| Titanium dioxide | 2 |
| Bisethylhexyloxyphenol methoxyphenyl triazine | 2 |
| Octocrylene | 7 |
| Ethylhexyl methoxycinnamate | 4 |
| Parabens | 1 |
| Antioxidants | 0.5 |
| Perfume | 0.5 |
| Water | ad 100 |

Impregnation solution 5: Sunscreen formulation

| Constituent | % by weight |
|---|---|
| Glyceryl stearate citrate | 6.5 |
| Glyceryl isostearate | 2 |
| Cetyl alcohol | 1 |
| Dicaprylyl carbonate | 5 |
| Shea butter | 3 |
| $C_{12-15}$ alkyl benzoate | 1 |
| Bisethylhexyloxyphenol methoxyphenyl triazine | 2 |
| Butylmethoxydibenzoylmethane | 1 |
| Ethylhexyl triazone | 2 |
| Phenylbenzimidazole sulfonic acid | 2 |
| Ethylhexyl methoxycinnamate | 4 |
| Glycerol | 10 |
| Tricontanyl PVP | 1 |
| Citrate buffer | 1 |
| Parabens | 1 |
| Antioxidants | 0.5 |
| Perfume | 0.5 |
| Water | ad 100 |

Impregnation solution 6: Sunscreen formulation

| Constituent | % by weight |
|---|---|
| Glyceryl stearate citrate | 2.5 |
| Cetyl alcohol | 1 |
| Dicaprylyl carbonate | 4 |
| Capric/caprylic triglyceride | 2 |
| $C_{12-15}$ alkyl benzoate | 6 |
| Methylene bisbenzotriazolyl tetramethylbutylphenol | 2 |
| Butyl methoxydibenzoylmethane | 2 |
| Ethylhexyl triazone | 4 |
| Bisimidazylate | 2 |
| Methylbenzylidene camphor | 4 |
| Glycerol | 5 |
| PVP hexadecene copolymer | 1 |
| Parabens | 1 |
| Antioxidants | 0.5 |
| Perfume | 0.5 |
| Water | ad 100 |

| Impregnation solution 7: Sunscreen formulation | |
| --- | --- |
| Constituent | % by weight |
| Ceteareth-20 | 7.5 |
| Glyceryl stearate citrate | 3 |
| Cetyl palmitate | 1.5 |
| Dicaprylyl carbonate | 5 |
| Cocoglycerides | 2 |
| $C_{12-15}$ alkyl benzoate | 6 |
| Barium sulfate | 2 |
| Bisethylhexyloxyphenol methoxyphenyl triazine | 2 |
| Ethylhexyl triazone | 4 |
| Bisimidazylate | 1 |
| Phenylbenzimidazole sulfonic acid | 2 |
| Methylbenzylidene camphor | 4 |
| PVP hexadecene copolymer | 1 |
| NaOH | 0.5 |
| Parabens | 1 |
| Antioxidants | 0.5 |
| Perfume | 0.5 |
| Water | ad 100 |

| Impregnation solution 8: Aftersun/skincare formulation | |
| --- | --- |
| Constituent | % by weight |
| Glyceryl stearate citrate | 2 |
| Cetyl alcohol | 1 |
| Dicaprylyl carbonate | 5 |
| Shea butter | 1 |
| Octyldodecanol | 3 |
| Cyclomethicone | 1 |
| Mineral oil | 2 |
| Ethanol | 5 |
| Parabens | 1 |
| Antioxidants | 0.5 |
| Perfume | 0.5 |
| Water | ad 100 |

That which is claimed:

1. A cloth, comprising a water-insoluble nonwoven, which has been moistened with an impregnation solution comprising an oil-in-water emulsion having a viscosity of less than 2000 mPa·s, and comprising:
one or more partially neutralized glyceride esters selected from the group consisting of monoglyceride and diglyceride esters of saturated fatty acids with citric acid and
one or more fatty alcohols selected from the group consisting of branched and unbranched alkyl alcohols with 10 to 40 carbon atoms.

2. The cloth as claimed in claim 1, wherein the weight ratio of the unimpregnated cloth to the impregnation solution is from 1:1 to 1:5.

3. The cloth as claimed in claim 1, wherein the one or more partially neutralized glyceride esters include glyceryl stearate citrate.

4. The cloth as claimed in claim 1, wherein the one or more fatty alcohols include cetyl alcohol, stearyl alcohol, or a mixture thereof.

5. The cloth as claimed in claim 1, wherein the one or more fatty alcohols include cetyl stearyl alcohol.

6. The cloth as claimed in claim 1, wherein the total amount of the one or more partially neutralized glyceride esters in the impregnation solution is from 0.1 to 10.0% by weight, based on the total weight of the impregnation solution.

7. The cloth as claimed in claim 6, wherein the total amount of the one or more partially neutralized glyceride esters in the impregnation solution is from 0.5 to 6.0% by weight, based on the total weight of the impregnation solution.

8. The cloth as claimed in claim 1, wherein the total amount of the one or more fatty alcohols in the impregnation solution is from 0.1 to 10.0% by weight, based on the total weight of the impregnation solution.

9. The cloth as claimed in claim 1, wherein the total amount of the one or more fatty alcohols in the impregnation solution is from 0.5 to 6.0% by weight, based on the total weight of the impregnation solution.

10. The cloth as claimed in claim 1, wherein the weight ratio of the one or more partially neutralized glyceride esters to the one or more fatty alcohols is from 7:3 to 3:7.

11. The cloth as claimed in claim 10, wherein the weight ratio of the one or more partially neutralized glyceride esters to the one or more fatty alcohols is from 2:1 to 1:2.

12. The cloth as claimed in claim 11, wherein the weight ratio of the one or more partially neutralized glyceride esters to the one or more fatty alcohols is about 1:1.

13. The cloth as claimed in claim 1, wherein the impregnation solution includes an oil phase and an aqueous phase, wherein the oil phase is present in the impregnation solution in an amount from 5 to 40% by weight, based on the total weight of the impregnation solution.

14. The cloth as claimed in claim 1, wherein the impregnation solution further comprises one or more auxiliaries, additives or active ingredients selected from the group consisting of moisturizers, waxes, surfactants, preservatives, antioxidants, dyes, plant extracts, UV filters, pigments, deodorant and antiperspirant active ingredients, dermatological active ingredients and perfumes.

15. The cloth as claimed in claim 1, wherein the oil-in-water emulsion comprises one or more fatty alcohols selected from the group consisting of branched and unbranched alkyl alcohols with 10 to 30 carbon atoms.

16. A cloth, comprising a water-insoluble nonwoven, which has been moistened with an impregnation solution comprising an oil-in-water emulsion having a viscosity of less than 2000 mPa·s, and comprising:
one or more partially neutralized glyceride esters selected from the group consisting of monoglyceride and diglyceride esters of saturated fatty acids with citric acid;
one or more fatty alcohols selected from the group consisting of branched and unbranched alkyl alcohols with 10 to 40 carbon atoms; and
one or more washing-acting surfactants having a HLB greater than about 25.

17. The cloth as claimed in claim 16, wherein the amount of water in the impregnation solution is less than about 80.0% by weight, based on the total weight of the impregnation solution.

18. The cloth as claimed in claim 16, wherein the weight ratio of the unimpregnated cloth to the impregnation solution is from 1:1 to 1:5.

19. The cloth as claimed in claim 16, wherein the one or more partially neutralized glyceride esters include glyceryl stearate citrate.

20. The cloth as claimed in claim 16, wherein the one or more fatty alcohols include cetyl alcohol, stearyl alcohol, or a mixture thereof.

21. The cloth as claimed in claim 16, wherein the total amount of the one or more partially neutralized glyceride esters in the impregnation solution is from 0.1 to 10.0% by weight, based on the total weight of the impregnation solution.

22. The cloth as claimed in claim 16, wherein the total amount of the one or more fatty alcohols in the impregnation solution is from 0.1 to 10.0% by weight, based on the total weight of the impregnation solution.

23. The cloth as claimed in claim 16, wherein the weight ratio of the one or more partially neutralized glyceride esters to the one or more fatty alcohols is from 7:3 to 3:7.

24. The cloth as claimed in claim 16, wherein the impregnation solution includes an oil phase and an aqueous phase, wherein the oil phase is present in the impregnation solution in an amount from 5 to 40% by weight, based on the total weight of the impregnation solution.

25. The cloth as claimed in claim 16, wherein the impregnation solution further comprises one or more auxiliaries, additives or active ingredients selected from the group consisting of moisturizers, waxes, preservatives, antioxidants, dyes, plant extracts, UV filters, pigments, deodorant and antiperspirant active ingredients, dermatological active ingredients and perfumes.

* * * * *

UNITED STATES PATENT AND TRADEMARK OFFICE
CERTIFICATE OF CORRECTION

PATENT NO. : 7,658,936 B2  Page 1 of 1
APPLICATION NO. : 10/745066
DATED : February 9, 2010
INVENTOR(S) : Von Der Fecht et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1624 days.

Signed and Sealed this

Thirtieth Day of November, 2010

David J. Kappos
*Director of the United States Patent and Trademark Office*

UNITED STATES PATENT AND TRADEMARK OFFICE
CERTIFICATE OF CORRECTION

PATENT NO.       : 7,658,936 B2
APPLICATION NO.  : 10/745066
DATED            : February 9, 2010
INVENTOR(S)      : Von Der Fecht et al.

It is certified that error appears in the above-identified patent and that said Letters Patent is hereby corrected as shown below:

Column 2,
Line 11, "DNV" should read --D/W--.

Column 4,
Line 23, "octyidodecyl" should read --octyldodecyl--
Line 58, "SAN" should read --S/W--.

Column 8,
Line 48, "(e.g. µmol to zmol/kg)" should read --pmol to µmol/kg--.

Column 17,
Line 15, "trimethylsiloxysilyl propyloxy" should read --trimethylsiloxysilylpropyloxy--.

Column 23,
Line 26, "*propionibactedum*" should read --*propionibacterium*--.

Signed and Sealed this
Twenty-first Day of June, 2011

David J. Kappos
*Director of the United States Patent and Trademark Office*